United States Patent [19]

Melton et al.

[11] Patent Number: 4,756,195
[45] Date of Patent: Jul. 12, 1988

[54] MODULUS OF ELASTICITY TESTER APPARATUS PARTICULARLY ADAPTED FOR TESTING COMPLIANT MATERIALS

[75] Inventors: David L. Melton; Keith E. Caudill, both of Fort Wayne, Ind.

[73] Assignee: ITT Aerospace Optical a division of ITT Corporation, Fort Wayne, Ind.

[21] Appl. No.: 934,363

[22] Filed: Nov. 24, 1986

[51] Int. Cl.[4] .............................................. G01N 3/22
[52] U.S. Cl. ...................................................... 73/847
[58] Field of Search ................. 73/847, 841, 842, 843; 324/158 F

[56] References Cited

U.S. PATENT DOCUMENTS

| | | | |
|---|---|---|---|
| 2,351,574 | 6/1944 | Sivertsen | 73/847 |
| 2,765,655 | 10/1956 | Scott | 73/847 |
| 2,986,031 | 5/1961 | Yorgiadis et al. | 73/847 |
| 3,122,915 | 3/1964 | Haller | 73/847 |
| 3,501,952 | 3/1970 | Gergen et al. | 73/847 |
| 3,611,795 | 10/1971 | Goldmann et al. | 73/843 |
| 4,476,727 | 10/1984 | Hawk et al. | 73/847 |
| 4,601,195 | 7/1986 | Garritano | 73/843 |

FOREIGN PATENT DOCUMENTS 171623  3/1966  U.S.S.R. ................ 73/847

Primary Examiner—Stewart J. Levy
Assistant Examiner—Robert R. Raevis
Attorney, Agent, or Firm—Robert A. Walsh; Thomas N. Twomey; Mary C. Werner

[57] ABSTRACT

Apparatus for measuring the modulus of elasticity of a sample specimen of a given thickness and area includes means for mounting one surface of the specimen on a rigid reference plane and an opposing surface of the specimen is then mounted on a rotatable surface. A torque arm coupled to the rotatable surface applies a predetermined torque which effectively causes this surface to rotate thereby twisting the specimen through a given angle. The angle is measured by means coupled to the rotatable surface, and based on the measured angle, one can calculate the modulus of elasticity in regard to the measured angle and in regard to the applied torque. The apparatus and methods essentially measure the modulus of elasticity through angular displacement of the specimen. The method and apparatus is particularly adaptable to measure the modulus of elasticity of a compliant layer associated with a printed circuit board which compliant layer acts as a stress relief layer for surface mounted components and solder joints coupling those components to the printed circuit board assembly.

6 Claims, 5 Drawing Sheets

MODULUS OF ELASTICITY TESTER APPARATUS PARTICULARLY ADAPTED FOR TESTING COMPLIANT MATERIALS

BACKGROUND OF THE INVENTION

This invention relates to a modulus of elasticity testing apparatus and associated methods for same. More particularly the invention is related to a method and apparatus for testing compliant materials for determining the modulus of elasticity of such materials used in printed circuit boards.

The modulus of elasticity is defined as the ratio of the unit stress to the unit deformation of a structural material and basically is a constant as long as the unit stress is below the proportional limit. The shearing modulus of elasticity is frequently called the modulus of rigidity and there are other moduli which are determinative of elasticity measurements.

As is known, elasticity is a property whereby a body when deformed automatically recovers its normal configuration as the deforming forces are removed. Each of the several types is probably due to the action of the intermolecular forces which are in equilibrium only for certain configurations. Deformation, or more briefly, strain, is of various kinds and in each case it is the measure of a certain abstract ratio. In any event, the modulus of elasticity has been utilized to determine the characteristics of various materials. Measurement equipment for determining the modulus of elasticity is utilized in the prior art and is utilized for a wide variety of materials.

As one can ascertain, various tables exist for different materials which give the modulus of elasticity for the material. In regard to such measurements, one is normally concerned with a quantity defined as Poisson's ratio which is equal to the relative lateral contraction divided by the relative longitudinal extension. Poisson's ratio for various materials is known and has been defined.

As indicated, the prior art utilized various modulus measuring mechanisms which are essentially employed to measure the stress relationship of materials, and from the stress strain curve the modulus of the material can be derived. In any event, in order to use such equipment, the material to be measured must be prepared into a standard sample configuration. This standard sample configuration which is of a particular length, width and thickness is utilized in conjunction with applied forces to determine the various moduli.

The methods used in the prior art employ a tensile force measurement rather than an angular displacement. Thus such prior art techniques require time consuming operations in regard to the preparation of the standard sample. The sample then may be placed in a tensile machine as between a pair of jaw vises and is stressed at given forces in order to measure the tensile stress or strength. These measurements essentially depict deformation of the material and hence the various moduli can be derived by suitable equations.

In any event, the theory of elasticity and the various parameters involved in regard to elasticity have been the subject matter of many articles and many textbooks. See for example, a textbook entitled *Introduction to Elasticity*, published by Holt, Rinehardt and Winston, New York 1964 by G. Nadeau. See also a text entitled *Theoretical Elasticity and Plasticity*, published by Thames and Hudson Company of London, England 1959 by D. E. R. Godfrey. It is indicated that the present invention is particularly directed for accepting compliant material for use with surface mounted devices as in coated printed circuit boards.

Essentially, as one can ascertain, in the semiconductor art surface mounted devices such as surface mounting connectors and components are widely employed, and there have been many articles written about the advantages of surface mounting. The surface mounted component is usually mounted on a printed circuit board and is positioned on the board by means of various solder joints which connect the surface mounted component to the board at various terminal areas.

When utilizing such printed circuit boards in conjunction with surface mounted components and solder joints, one experiences a particular problem in regard to temperature changes. The problem is that the surface mounted components have widely different temperature coefficients from those of the printed circuit board. The printed circuit boards which are typically made from a glass epoxy material exhibit larger expansion coefficients than the surface mounted components.

Hence as one can ascertain, during temperature cycling of the assembly, the printed circuit board tends to expand at a greater rate than the surface mounted components. This causes unusual stresses in the solder joints and by constant temperature cycling one can actually fatigue the solder joints, resulting in a complete failure of the printed circuit module.

In any event, in order to circumvent such temperature problems, various manufacturers have employed coatings sometimes referred to as a "butter coat". These coatings constitute a relatively thin film of a compliant or elastomeric material such as a rubber type material which is coated over the board. The thickness of such layers is between 5/1000 to 10/1000 of an inch. The compliant coating acts as a shock absorber and essentially functions to dissipate the energy would otherwise be coupled directly to the solder joints. In regard to this technique, the use of the elastomer serves to protect the board during large temperature cycling operations.

It is a problem in regard to the particular user of such an assembly to determine what the modulus of elasticity is so one can ascertain that the boards will operate over the required temperature range. It is desirable that the composite structure which consists of the printed circuit board and the compliant layer or elastomeric layer is capable of matching and providing proper thermal expansion characteristics when utilized in conjunction with a surface mounted chip carrier or a component circuit board.

As indicated, the present technique for accepting compliant material for use with surface mounted devices is performed by thermal cycling test coupons. A test coupon is a test device which is exactly the same size and thickness as the resultant printed circuit board. This method is extremely costly and takes several weeks to be completed before the compliant material is accepted from the vendor. The exact nature of the particular problem and the solution thereof will be subsequently explained. Except, suffice it to say that there is a need to develop acceptance methods for complaint materials based on the material's physical properties. In addition a method and apparatus was needed to correlate thermal cycles to failure with physical material properties measured at incoming acceptance for each received lot of material.

The method and apparatus also will serve to eliminate making and preparation of complicated sample forms in regard to length, width and thickness, as will be further explained.

It is therefore an object of the present invention to provide a modulus of elasticity tester apparatus for compliant materials.

It is a further object of this invention to provide a modulus of elasticity tester for enriched resin compliant layer substrates employed in surface mounted printed circuit board applications.

It is a further object of this invention to provide a method for measuring the modulus of elasticity in compliant layer materials.

It is a further object of the present invention to provide a modulus of elasticity measurement apparatus and method for measuring the modulus of elasticity by responding to small angular deflections of the compliant layer without the necessity of processing material into a printed circuit board test coupon as for example implemented by the prior art.

BRIEF DESCRIPTION OF THE PREFERRED EMBODIMENT

Apparatus for measuring the modulus of elasticity of a sample specimen of a given thickness and area comprising means for mounting one surface of said specimen on a rigid reference plane and an opposing surface of said specimen coupled to a rotatable surface, torque exerting means coupled to said rotatable surface and operative to apply a force to said surface to tend to twist said specimen through an angle, means coupled to said rotatable surface for measuring said angle for determining the modulus of elasticity in regard to said force as applied to said torque means and said angle.

DETAILED DESCRIPTION OF THE FIGURES

Figure 1:
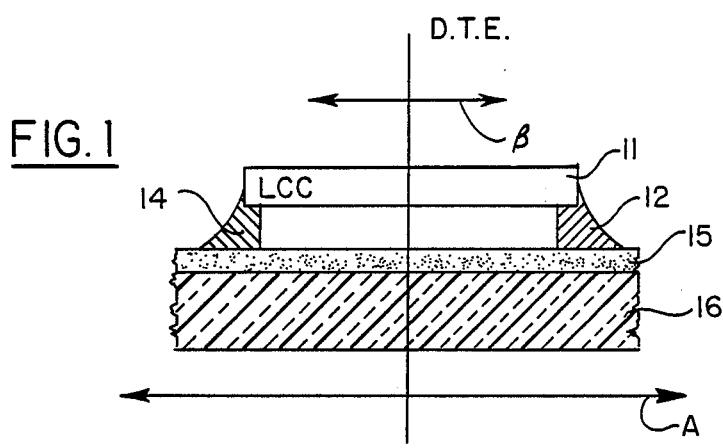
FIG. 1 is a side partial cross sectional view of a printed circuit board employing a compliant layer utilized for surface mounting components.

Referring to FIG. 1, there is shown a printed board assembly which is particularly useful with surface mounted components.

Essentially, as one can ascertain from FIG. 1, there is shown a printed circuit board 16 which is a conventional printed circuit board. Printed circuit boards are widely employed and are available in thicknesses varying from 1/64 to ½ inch. There have been various materials utilized in the prior art to provide printed circuit board configurations such as the board 16. These are known as the Nema type XXP paper base phenolic boards. The Nema type FR2, which is a paper base phenolic board, the Nema type FR3, a paper based epoxy board and the Nema type FR4 which is glass fabric base epoxy. In any event, there are various materials which have been employed for implementing the printed circuit board including glass, cloth, Teflon, silicon, rubber, glass mat polyester resin laminate, Teflon film and so on. Examples of various types of printed circuit boards can be had by referring to a text entitled *Reference Data for Radio Engineers*, published by Howard W. Sams and Co., a subsidiary of ITT Corp. and generally shown in Chapter 5, on pages 5-32 to 5-35. In any event, printed circuit boards are well known.

Shown coating the top surface of the printed circuit board is a relatively thin layer of a compliant material 15. The material 15 is available from many sources and is an elastomeric material such as a liquid rubber or other flexible compound. The material 15 is directly attached to the printed circuit board 16. As indicated the printed circuit board utilized herein is of the above-noted FR-4 type, although other types of printed circuit boards can be employed as well.

Essentially, the compliant layer 15 addresses the problem of thermal coefficient of expansion mismatch by providing a strain relief medium between the printed circuit board substrate 16 and the surface mounted components such as the LCC or Leadless Chip Carrier module 11. As seen, module 11 is secured to the printed circuit board 16 by means of conventional solder joints 12 and 14. The above problem regarding thermal coefficient of expansion results in the following.

During a temperature cycling, the printed circuit board 16 expands more rapidly than does the carrier chip 11. This is shown essentially by arrows A and B which in a diagrammatic form show that the printed circuit board 16 expands more rapidly than does the carrier chip 11 over the same temperature range. Without the compliant layer 15, the differential rates of expansion or the differential thermal expansion (D.T.E.) causes large stresses in the solder joints. This especially occurs during temperature cycling whereas the temperature is continuously raised and lowered. This difference in thermal expansion causes the solder joints which carry the carrier chip 11 to fatigue and eventually result in the complete destruction of the solder joint.

As indicated, the carrier chip 11 is a surface mounted component and for example could be any type of surface mounted component including a connector, an integrated circuit chip, a discrete component and so on. Many examples of surface mounted components are available from many sources. Typically, there may be a difference of 2 to 1 whereby the printed circuit board 16 attempts to expand for a temperature rise twice as much as the component carrier board 11. As one can understand this causes stresses. By utilizing a compliantlayer or an elastomeric layer as 15, one addresses the problem of thermal coefficient of expansion mismatch by providing a strain relief medium between the substrate and the components. The compliant layer offers strain relief by absorbing the strain energy generated by the thermal cycling at extreme temperatures, thus effectively reducing the strain energy in the solder joints as 12 and 14. The compliant layer approach provides a reliable method of surface mounting devices utilizing conventional PCB substrate manufacturing processes. These processes are also well known.

As is understood, the ability to survive a certain number of thermal cycles using the compliant layer approach is dependent upon the following characteristics. First, it is a function of the leadless chip carrier (LCC) size. Second, it is also a function of the particular solder joint quality and characteristics. Third, it is also a function of the quality of the compliant layer. The quality of the compliant layer is determined by the compliant materials effective modulus of elasticity (E). Such compliant layers are available from many manufacturers, and essentially the layer is sometimes referred to as a "butter coat". These layers can be between 0.005 to 0.007 inches thick or more, and essentially includes an elastomeric material such as a rubber which acts as a shock absorber as explained above.

The effective modulus of elasticity as used herein relates to the stress developed in the compliant layer 15 to the strain in a region beyond the initial yield point of the material.

Figure 2:
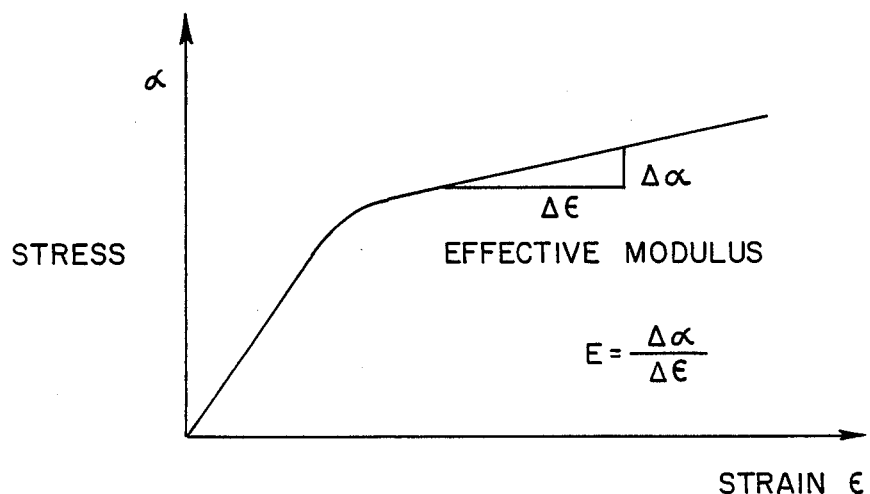
FIG. 2 is a graph depicting stress for strain in order to explain the derivation of modulus of elasticity.

Referring to FIG. 2, there is shown a typical graph depicting strain as the horizontal axis and stress as the vertical axis. The modulus of elasticity (E) is equal to a differential change in stress divided by a differential change in strain.

FIG. 2, basically, is an illustration of the effective modulus of elasticity (E) of the material. As one can also ascertain from elementary physical considerations, when one discusses elasticity, one is concerned with various moduli. For example, the elongation of a rod under tension is expressed as the ratio of the increase in length to the unstretched length. Linear compression is the reverse of elongation. Both are accompanied by a fractional change in diameter the ratio of which to the elongation is called the Poisson ratio. Shear is a strain involving a change of shape such that an imaginary cube traced in the unstrained material becomes a rhombic prism. The measure of shear is the tangent of the angle through which the oblique edges have been made to depart from their original perpendicular direction.

Volume strain is the ratio of a decrease in volume to the normal volume. Flexure or bending and torsion or twisting are combinations of these more elementary strains. The theory of elasticity as indicated above is widely known and many texts and articles depict the various moduli and the various nature of such moduli. Essentially, for each type of stress and strain there is a modulus which is the ratio of the stress to the corresponding strain. In the case of elongation or linear compression it is commonly called Young's modulus. There is also the bulk modulus and the shear modulus of rigidity and such moduli are also equated to the modulus of elasticity.

Figure 3:
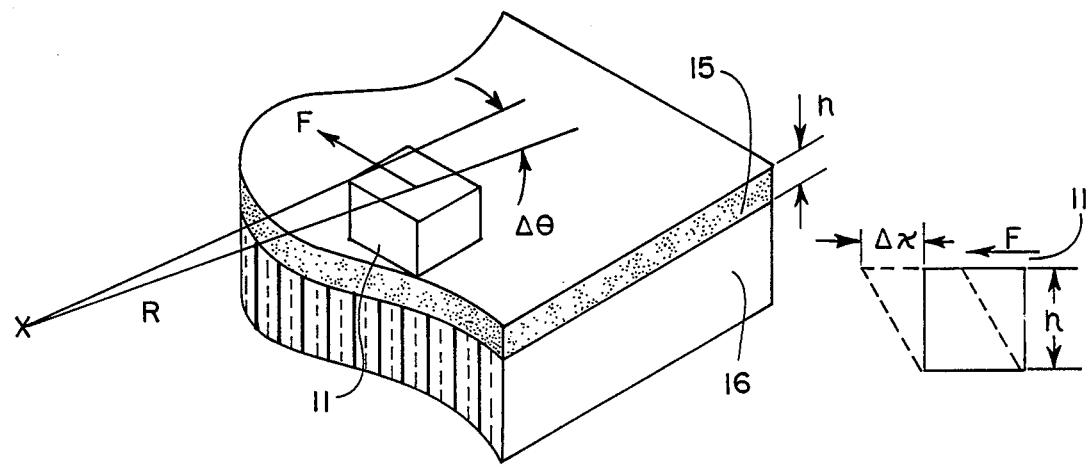
FIG. 3 is a partial cross sectional diagram depicting a printed circuit board having a compliant layer which is subjected to a force according to the teachings of this invention.

Referring to FIG. 3, there is shown a diagrammatic view of a partial cross section of the effective printed circuit board together with a component represented by a solid rectangle and referred to by the reference numeral 11 to indicate a carrier chip such as that chip shown in FIG. 1.

The printed circuit board is represented by numeral 16 as shown in FIG. 1, while the compliant layer is represented by numeral 15. As can be seen by FIG. 3, the compliant layer is assumed to have a thickness of h. There is a force F which is parallel to the top surface of the carrier chip 11. Torque is exerted thru a point X with a moment arm R distance from the force.

Adjacent to FIG. 3, there is shown a small representation of the deformation of the unit 11 by a force F whereby the original square or rectangular cross section of the unit 11 is changed by the force F into a rhombus. The above nature of the deflecting force F having a tendency to deform the member 11 into the rhombic has been described above. Based on the considerations and the various items shown in FIG. 3, the following mathematical equations are indicative of the nature of the method utilized herein and are instrumental in considering the theory and the structure developed by the theory. Hence the following mathematical equations are applicable to FIG. 3 as will be further described.

Essentially, referring to FIG. 3 a torque is applied to the composite structure shown in FIG. 3 or an angle designated by $\Delta\theta$ is applied and then either the angle or the torque is measured according to the following equation.

Apply $T$    Apply $\theta$
MEASURE $\theta$  or  MEASURE $T$ where
T = Applied Torque (in lbs.)
$\theta$ = Angle of Twist (Radians)

$$\theta = \frac{\gamma L}{R} \quad (1)$$

where
$\theta$ = Angle Twist (radian)
$\gamma$ = Shear Strain
L = Total thickness of all compliant material (IN)
R = Radius of sample size (IN)
Shear strain is related to shear stress by $$\gamma = \frac{\tau}{G} \quad (2)$$

where
$\tau$ = Shear Stress (lb/IN$^2$)

$$G = \text{Modulus of Rigidity (lb/IN}^2) \quad (3)$$
$$= \frac{E}{2(1 + M)}$$

where
E = Modulus of Elasticity (lb/IN$^2$)
$\mu$ = Poisson's Ratio
$\mu$ = Lateral Strain/Axial Strain
Shear Stress ($\tau$) under torsional loading for a circular sample configuration is related to applied torque (T) by $$\tau = \frac{TR}{J} \quad (4)$$

where
J = Polar moment of inertia for sample configuration which $= \pi R4/2$ for circular sample
L is related to individual compliant layer sample thickness by $$L = Nh \qquad (5)$$

where
N = Number of compliant layers measured
h = Sample compliant layer thickness (inch)

The effective modulus E as defined in FIG. 2, is the slope between two separate points in the region above the initial yield point. Combining equations (2), (3), (4), and (5) into equation (1) then $$\Delta\theta = \frac{4Nh(1 + \mu)\Delta T}{\pi R^4 E}$$

where
$\Delta$ = Difference in two applied torque values
$\Delta\theta$ = Angular difference As one can see from the above analytical relationships, the angle $\Delta\theta$ is inversely proportional to the modulus of elasticity. Hence by knowing the angle or by knowing the applied torque, one can determine the modulus of elasticity from the equation shown.

As will be explained, according to the above-noted analysis, one can now accurately measure the modulus of elasticity for sample material. Specifically, a small sample of the material as received is used as a sample and one can accomplish the measurement of the effective modulus of elasticity by the following method and apparatus. The quality of the raw material is then determined and the expected performance of the final printed circuit board is predicted from this quality. These measurements can be performed at incoming inspection according to the described procedures and the particular material specification. The measurement used herein is an angular displacement as one can ascertain from FIG. 3.

Hence with the method developed, the measurement can be taken directly from the incoming material without detailed processing and the value for the modulus determined directly from the measured displacement. The method provided by this invention is extremely simple and relates to angular displacement developed under shear to the material property of the compliant layer just as it would be stressed under shear under the thermal cycling environment.

The method described herein is extremely applicable to surface mounted applications although it can be also utilized for conventional modulus measurement methods.

Figure 4:
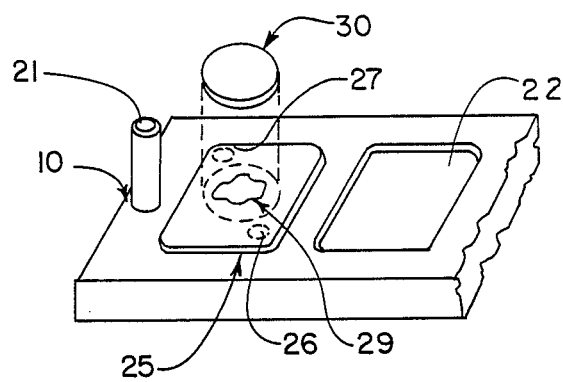
FIG. 4 is a partial perspective plan view of a test fixture used for specimen preparation.

Reference will now be made to FIG. 4. Essentially, as will be explained, there will be described the detail for testing of the modulus of elasticity of printed wiring laminate sheets which are coated with a compliant layer or an elastomeric material or having an enriched resin on a top surface.

Referring to FIG. 4, there is shown a partial sectional plan view of a test fixture 20. The test fixture 20 has a plurality of recesses as 22 on the top surface. Each is of a predetermined dimension. Essentially, as shown in FIG. 1, the test fixture 20 has an upstanding post 21 and possesses one such post on each side as further evidenced by referring to FIG. 5.

Shown in FIG. 4, is a backer plate 25. Essentially, the backer plate 25, as will be further explained, may be fabricated from a suitable metal or other material. The backer plate 25, as seen, has two apertures located thereon as 26 and 27, one on opposite corners of the rectangular shaped backer plate. The backer plate is dimensioned to fit into the aperture as 22 located on the top surface of the test fixture 20.

Shown positioned central to the backer plate is a spot or an area to which is applied an adhesive 29. The adhesive 29 may be a conventional adhesive such as the type sold and distributed by a company called Loctite which markets an adhesive known as Super Bonder 496. Any suitable adhesive such as typical epoxies and so on can be employed. Shown positioned above the adhesive area 29 is a laminate 30. Essentially, the laminate consists of a test sample which has been removed from typical laminated printed circuit board material. The test sample as shown is circular in dimension but can be of any shape.

In particular and as will be further explained, representative test samples 30 are approximately 1 inch in diameter and are taken from the laminate material and mounted to the backer plate which is positioned in the aperture 22 of the bottom test fixture 20 as shown in FIG. 4. After the appropriate specimen 30 has been removed from the received laminate material, one then utilizes a 400 grit sand paper to score or abrade the copper terminal areas associated with the printed circuit laminate 30. This is done prior to securing the wafer to the adhesive, and enough adhesive is applied so that a good bond is achieved around the perimeter of the laminate sample.

Figure 5:
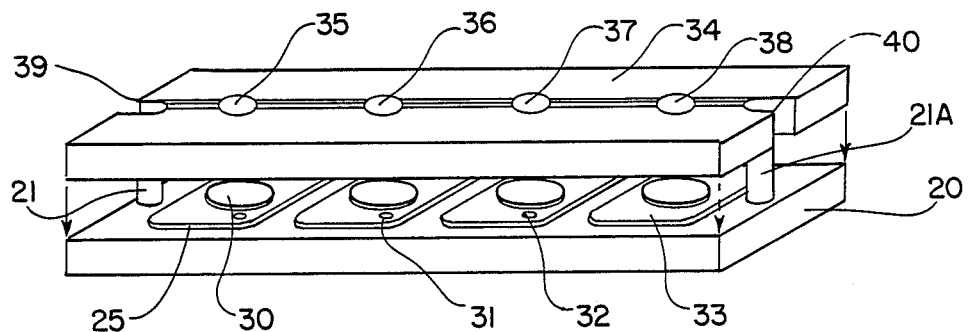
FIG. 5 is a partial plan view of a complete test fixture apparatus used for sample preparation.

Referring to FIG. 5, there is shown the bottom portion of the test fixture 20 which contains four samples as for example the samples shown in FIG. 4. The samples each have a backer plate as 31, 32 and 33 associated with the samples and each has a laminate specimen as specimen 30 secured to the backer plate by means of an adhesive. A top fixture portion 34 is shown. This top portion contains four apertures as 35, 36, 37 and 38, each associated with the laminate mounted on the backer plate which are maintained in the bottom fixture. The top fixture 34 has two side apertures as 39 and 40 which serve to surround the posts as 21 and 21A. After the laminate 30, for example has been emplaced on the backer plate 25 by means of the adhesive, the top fixture portion which is made of a relatively heavy metal is emplaced as shown in FIG. 5 and as more clearly shown in FIG. 6 in a side view on top of the fixture 20 and is allowed to remain for a suitable time to allow the adhesive to firmly bond the sample 30 to the backer plate 25.

Figure 6:
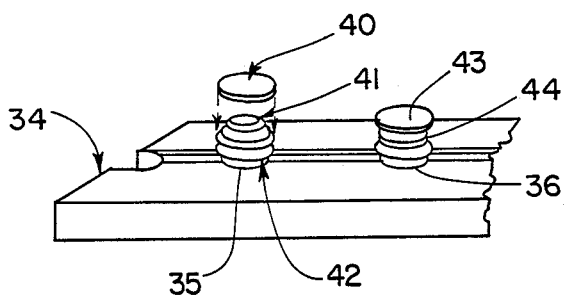
FIG. 6 is a side view showing a sample being accommodated by the test fixture of FIG. 5.

In this manner the entire fixture is set up as shown in FIG. 6 for all prepared samples and is allowed to remain until the adhesive 29 has had a suitable time to harden or cure. The next step in the process is to prepare a second test sample which is approximately ½ inch in diameter.

Figure 7:
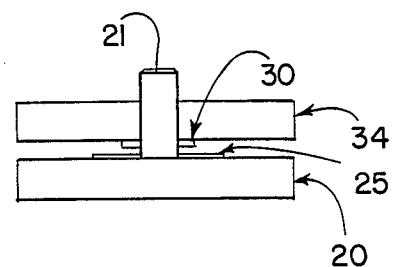
FIG. 7 is a partial plan view showing a top portion of a test fixture according to this invention.

Referring to FIG. 7, there is shown a portion of the top test fixture 34. A torque socket member as member 42 is emplaced in aperture 35 associated with the top fixture member 34. The torque socket member 42 is made from a suitable metal and has a central peripheral area which is reinforced. The torque socket member 42 may be threaded at one end as inserted into aperture 35. Shown adjacent the torque socket member 42 is an identical torque socket member 44 which is associated with aperture 36. Also shown positioned above the torque socket member is an additional sample of laminate material 40.

Figure 8:
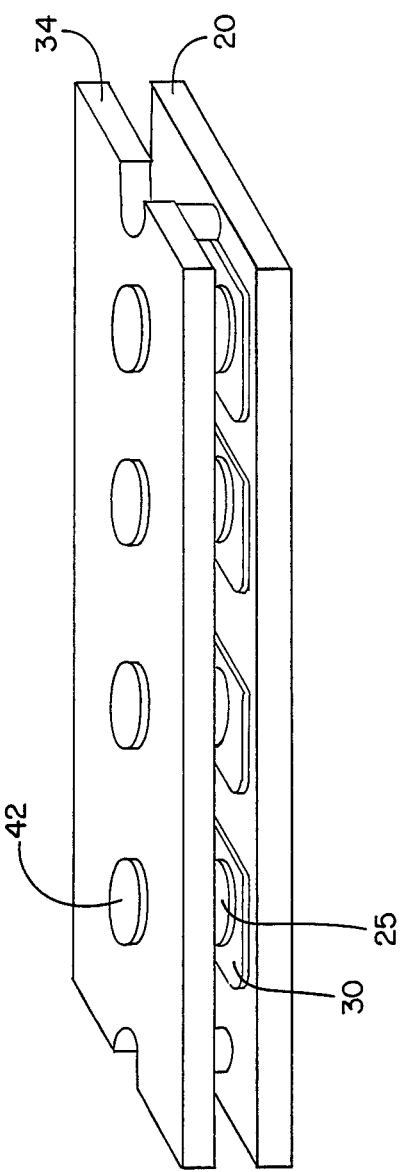
FIG. 8 is a plan view of a test fixture for sample preparation.

As indicated above, this sample 40 is essentially ½ inch in diameter. The peripheral area 41 of the torque socket member 42 is coated again with a suitable adhesive such the adhesive described above, and the member 40 is emplaced upon the area 41. Shown adjacent is another sample member 43 which has been secured to the associated torque socket member 44. Thus after placement of all the ½ inch diameter laminate pieces as 40 and 43, the adhesive is applied at the laminate interfaces and the top fixture 34 is flipped over as shown in FIG. 8. In this manner the two laminate pieces are brought together. Adhesive is applied to secure the laminate pieces together as for example shown in FIG. 9.

Figure 9:
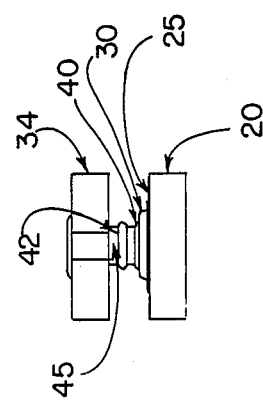
FIG. 9 is a side view depicting the test fixture and specimen accommodated.

Thus as one can see from FIG. 9, the top fixture section 34 is emplaced upon the bottom fixture section 20 which contains the backer plate 25 having the laminate of 1 inch diameter secured thereto by means of an adhesive. The top fixture plate having the torque socket 42 positioned in the corresponding aperture has the smaller diameter laminate 30 secured thereto. Adhesive is emplaced between the two laminate sections to therefore secure the top laminate to the bottom laminate. The entire unit or assembly is allowed to remain in this position for a requisite time period to allow the adhesive between the laminate interfaces to cure, assuring the bonding of one laminate to the other.

Figure 10:
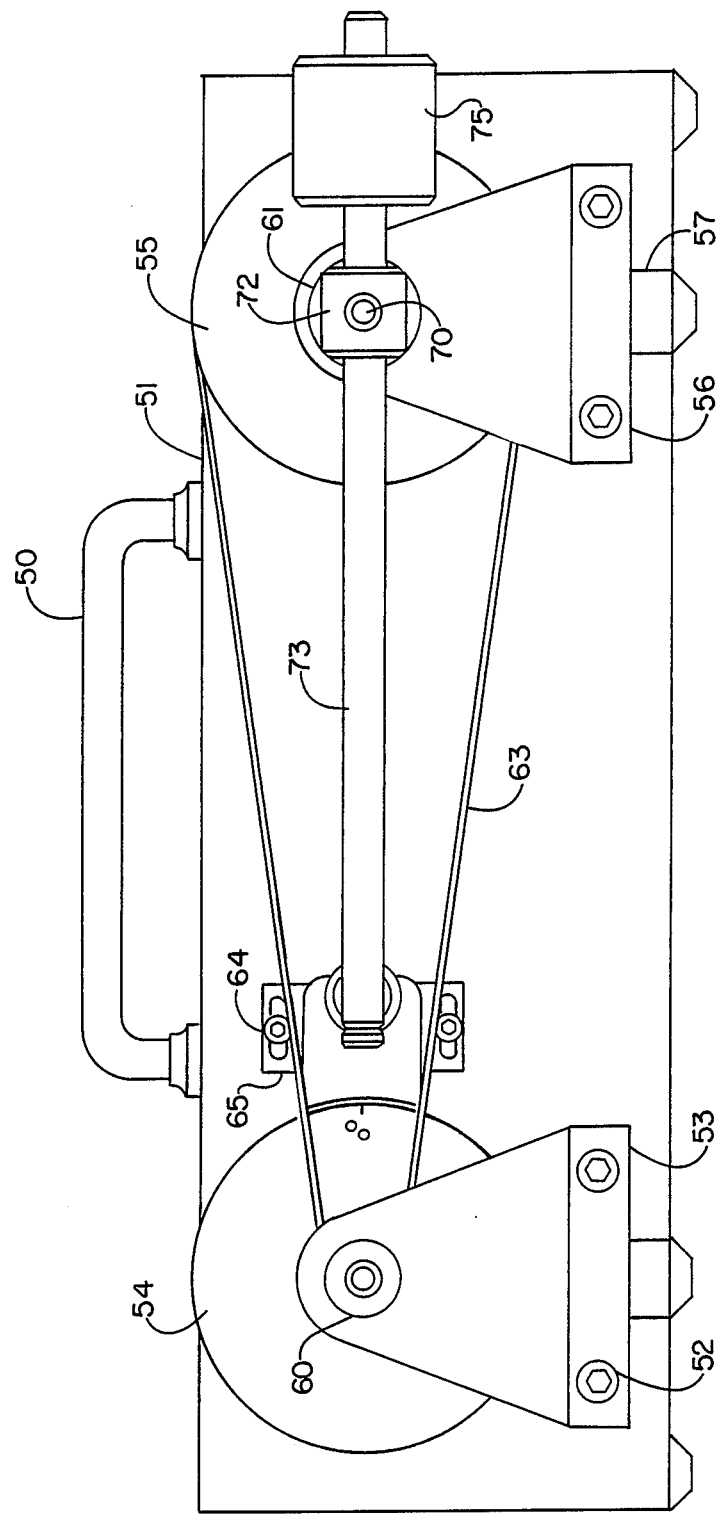
FIG. 10 is a front plan view of a test fixture apparatus according to this invention.

The next step in the procedure is now to remove the torque member 42 from the aperture in the top test fixture. The torque member will have secured to it the laminate 30, the laminate 25 and the backer plate. This constitutes the entire assembly which is then inserted into a modulus tester as shown in FIG. 10. As one can ascertain from FIG. 9, the top surface of the torque member 42 has a slot as 45 directed across the top surface. As will be further explained, the torque member having the backer plate and the dual laminate structure secured thereto is placed in the modulus tester apparatus 50 shown in FIG. 10.

FIG. 10 is a front view of the modulus tester 50, and briefly, the operation will be explained. The modulus tester 50 includes a housing which may be a rectangular type housing 51. As will be explained, the apparatus to be described is extremely simple to construct. Essentially, mounted to the housing are two bearing blocks designated by numerals 53 and 56. The bearing blocks are secured to the housing by means of conventional hexagonal screws 52 and are spaced from the bottom of the housing by means of spacers as spacer 57. Each bearing block contains a ball bearing assembly as 60 and 61 to enable easy rotation, and each bearing block accommodates a gear as gear 55. The bearing block 53 also accommodates an index wheel 54 which is graduated in terms of degrees as for example from 0° at the center point to 20°.

The reason for a graduation of 0° is due to the types of angles that would be measured by the technique. The gear as 55 and the smaller gear associated with the bearing 53 are coupled together by means of an endless belt as a sprocket chain or pitch chain 63. The gear 55 is 5 times the diameter of the gear associated with bearing block 53 and hence there is a 5 to 1 reduction in gear ratio.

Associated with the bearing block 56 is central shaft 70 which shaft 70 is associated with an accommodating nut 72 having a central aperture for supporting and carrying an extended torque arm 73. The arm 73 has a counter-balance or weight 75 positioned on the right side whereas on the left side of the arm there is room to emplace additional weights. The gear mechanism or bearing assembly 53 which is associated with the index dial 54 has adjustable means as 65 to enable one to adjust the proper tension in the belt.

As will be explained in regard to FIG. 10, weights are emplaced at the end of the torque shaft 73. The above-noted torque socket together with the back plate and respective laminates are emplaced in the mechanism behind the gear 55. Weights are then placed upon the end of the torque shaft 73 and remain there for predetermined time intervals. During each of these time intervals, the angular notation on the index mechanism associated with bearing plate 53 is noted and written down as will be explained.

Figure 11:
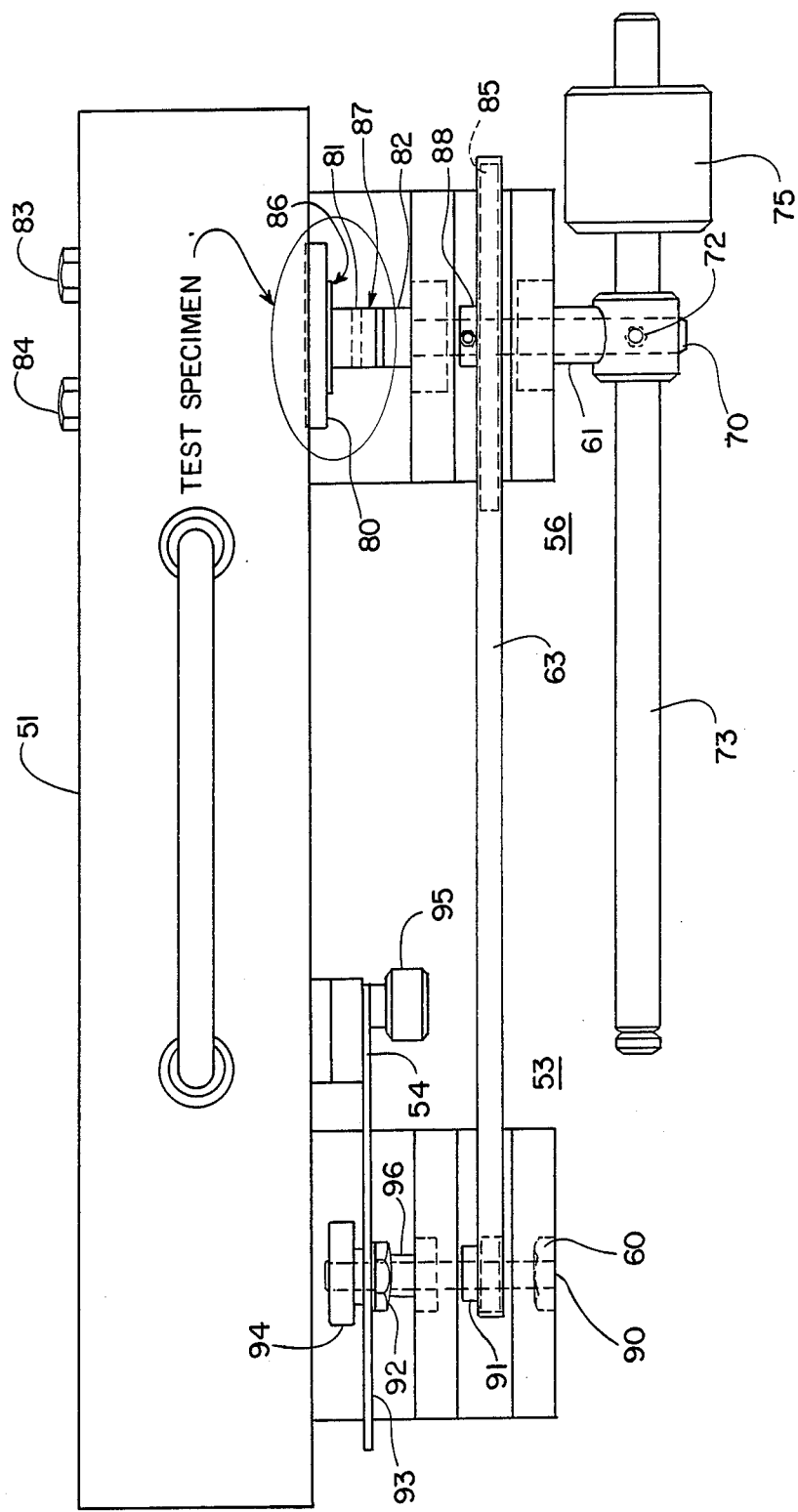
FIG. 11 is a top plan view of the test fixture apparatus of FIG. 10 when accommodating a specimen.

Referring to FIG. 11, there is shown a top plan view of the apparatus of FIG. 10. The backer plate is designated by reference numeral 80 and is the same backer plate as for example plate 25 of FIG. 9. The backer plate has secured thereto, as indicated above, the specimen 86 which consists of the two laminates which are also coupled to the torque socket member 81. As indicated above, the torque socket member 81 has a top slot which essentially is positioned in an extending flange which is coupled to the shaft 70 by means of a suitable coupling arrangement 88. The flange end of the shaft 82 is much like a screw driver and fits in the slot associated with the torque socket 81.

FIG. 11 also clearly shows the exact nature of the torque arm 73 and the counter balance 75. Shown in dashed lines is the gear 55 and the smaller gear 91. Both gears are associated with the chain 63 and both are associated with suitable roller bearing assemblies as assembly 60 and the top bearing assembly each associated with the respective bearing blocks as 53 and 56. All components as indicated above are well known in the art.

There is also shown a typical gear clamp 94 associated with the bearing block 53 and suitable spacers such as spacer 96 which is also associated with a clamp hub 93. The dial plate 93 is associated with a suitable dial mechanism located on the front to show degrees as explained before. The mechanism 95 is a thumb screw which will enable one to adjust the mechanism with respect to the tension in the chain 63.

As a further point, the backer plate as indicated above has two apertures which apertures contain bolts 83 and 84 which essentially hold the backer plate as shown between the bearing plate and the back surface of the housing 51.

As seen from FIG. 11, as the torque arm 73 rotates, there is a force exerted by means of the shaft 82 on the elastomeric member which is 86 which is secured to the backer plate which causes the member to twist or undergo an angular displacement. The exact angle of twist or the angle of displacement is read directly from the dial 54 associated with the left bearing assembly 53 and hence the exact number of degrees can be determined by the test equipment shown. It is noted that the test equipment is relatively simple and is a free wheeling device and operates in the following manner when a test is to be conducted.

By referring to FIG. 11, there is shown the entire sample assembly which is situated between the surface of the test fixture 51 and coupled to the shaft 70 associated with the bearing plate 56. The torque arm 73 has a counter-balance 75 and is held on shaft 70 by the nut 72. Tests are performed in the following manner. First, the torque arm 73 is counter balanced to eliminate any variation in test results due to torque arm loading. The indicator scale 54 is set to the zero position. The modulus tester with the specimen in place as shown in FIG. 11 is now ready to make elasticity measurements according to the following test method.

The first thing that is done is that one applies a 1 pound 9 ounce weight to the torque arm on the left side thereof. The following measurements are made for this weight emplaced on the torque arm. A measurement is made of the angle at 30 seconds then at 1 minute, then at 2 minutes, then at 3 minutes, then at 4 minutes and then at 5 minutes. This data is recorded and the angle displacements at the above-noted time intervals are entered on a data sheet. The average of these 1 pound 9 ounce deflection values is indicated as the angle $\theta1$. After the last value is recorded, an additional 1 pound 9 ounce weight is added to the 1 pound 9 ounce weight, and one then records the angular displacements at $5\frac{1}{2}$ minutes, 6 minutes, 7 minutes, 8 minutes, 9 minutes and 10 minutes. These angular displacements are again recorded on a typical data sheet for the 3 pound 2 ounce total combined weight. The average of these 3 pound 2 ounce deflections is indicated and determined and is designated as angle $\theta2$. The modulus of elasticity is then calculated from the following equation.

$$E = \frac{4Nh(1 + \mu)(T_2 - T_1)}{\pi R^4 \left( \frac{\theta_2}{5} - \frac{\theta_1}{5} \right)}$$

where:
h=Laminate thickness
$\mu$=Poisson's ratio=0.25
$T_2$=18.75 in-lbs.
$T_1$=9.375 in-lbs.
N=No. of contact pads=1
R=Radius sample size=0.25
$\theta_1, \theta_2$=Measured angular displacements
(Note: Convert angular degrees to angular radians)

The above-noted equation has been derived from the previous equation derived and shown in conjunction with FIG. 3. It is noted that each of the angles have been modified by a factor of 5 which essentially is directly related to the gear ratio of 5 to 1. Poisson's ratio is assumed to be 0.25 which is an extremely good approximation for all types of elastomeric materials. The torque T2 is equal to 18.75 inch pounds, while the torque T1 is equal to 9.375 inch pounds as shown in the above-noted table. This is strictly due to the above-noted weights in conjunction with the length of the arm 73. All other factors are fixed and are a function of the particular size of the unit.

It is, of course, understood that all these dimensions are given by way of example as for example utilized in actual equipment and may vary accordingly. As one can ascertain, the nature of the measurement is a function of the various lengths and diameters as described above, but can be varied accordingly and hence the torque arm 73 can be of any length desired. It is further indicated that the weights as placed on torque arm can be any weights as all these mechanical constraints can be ascertained by reviewing the above noted equations.

As one will understand from the above, the method and apparatus provided by the structure is simple and relates to the angular displacement developed under shear which displacement is measured by the equipment. The displacement defines the material properties of the compliant layer and in the exact manner as it would be stressed under shear during a thermal cycling environment. The method is particularly adaptable to surface mounted applications. Although the method can also be utilized to measure the modulus of elasticity of any elastomeric surface.

Many modifications and alterations will become obvious to those skilled in the art when reviewing the above-noted specification, and such modifications and alternatives are deemed to be encompassed within the spirit and scope of the invention as defined by the claims appended hereto.

What is claimed is:

1. A method of determining the modulus of elasticity of composite printed circuit board specimens having a substrate covered on one surface with a thin layer of compliant material which is used to provide thermal strain relief for solder joints coupled to components mounted on said compliant surface layer comprising:
   mounting the substrate of a first specimen on a rigid reference plane such that the compliant surface layer is facing outward;
   mounting the substrate of a second specimen on a torque arm which is rotatable such that the compliant surface layer is facing outward;
   securing the compliant surface of said first and second specimens together;
   rotating said torque arm with a predetermined amount of torque to cause said specimens to twist through an angle $\Delta\theta$ according to the magnitude of said torque;
   measuring said angle and calculating the modulus of elasticity from said angle and said torque.

2. The method according to claim 1, wherein the step of calculating said measured angle is afforded by means of the following equation:

$$\Delta\theta = \frac{4Nh(1 + \mu)/\Delta T}{\pi R^4 E}$$

where:
$\Delta\theta$=angle
E=effective modulus of elasticity
$\Delta T$=applied torque
h=thickness of specimen
$\mu$=Poisson's ratio for specimen
N=number of layers of specimen tested
R=radius of sample compliant material 3. The method according to claim 2, wherein said printed circuit board is a glass epoxy board with said compliant layer being an elastomeric layer of between 0.005–0.010 inches thick.

4. The method according to claim 3, further including the steps of:
   first securing the bottom surface of said printed circuit board to a backer plate,
   then securing said backer plate to said rigid reference plane.

5. The method according to claim 4, wherein the step of rotating said torque arm includes rotating said arm by means of an elongated rod of a given length coupled to said torque arm and applying a predetermined weight to said rod to cause said arm to rotate.

6. The method according to claim 5, wherein said specimens are circular in area.

* * * * *